United States Patent [19]

Michaelson et al.

[11] Patent Number: 4,533,772

[45] Date of Patent: Aug. 6, 1985

[54] PROCESS FOR DIRECTLY HYDROXYLATING OLEFINS USING AN OSMIUM-HALIDE CATALYST AND OXYGEN OXIDANT

[75] Inventors: Robert C. Michaelson, Waldwick; Richard G. Austin, Ridgewood, both of N.J.

[73] Assignee: Exxon Research & Engineering Co., Florham Park, N.J.

[21] Appl. No.: 527,352

[22] Filed: Aug. 29, 1983

Related U.S. Application Data

[63] Continuation-in-part of Ser. No. 310,217, Oct. 9, 1981, abandoned.

[51] Int. Cl.$^3$ ............ C07C 29/03; C07C 35/06; C07C 35/14; C07C 35/20

[52] U.S. Cl. .................... 568/860; 549/243; 560/186; 562/587; 568/811; 568/821; 568/833; 568/838; 568/847; 260/397.2

[58] Field of Search ............... 568/860, 833, 811, 821, 568/838, 847; 562/587; 560/186; 260/397.2; 549/243

[56] References Cited

U.S. PATENT DOCUMENTS 2,773,101 12/1956 Smith et al. .................. 568/860
3,335,174 8/1967 Norton ........................ 568/823

*Primary Examiner*—J. E. Evans
*Attorney, Agent, or Firm*—Robert A. Maggio

[57] ABSTRACT

The process for hydroxylating olefins with oxygen in the presence of water, an osmium-halide (e.g., OsBr$_3$) catalyst and transition metal containing co-catalyst (CuBr$_2$) is disclosed.

45 Claims, No Drawings

PROCESS FOR DIRECTLY HYDROXYLATING OLEFINS USING AN OSMIUM-HALIDE CATALYST AND OXYGEN OXIDANT

CROSS-REFERENCE TO RELATED APPLICATION

The present application is a continuation-in-part application of U.S. patent application Ser. No. 310,217 filed Oct. 9, 1981, now abandoned, the disclosure of which is herein incorporated by reference.

BACKGROUND OF THE INVENTION

The present invention relates to processes for hydroxylating olefins in the presence of a specifically defined catalyst and oxidant combination.

Processes for the production of glycols such as ethylene glycol, from olefins are well known in the art.

For example, it is well known from the technical literature and patents that olefins can be effectively oxidized with a strong oxidizing agent in the presence of catalytic amounts of specific osmium oxide containing compounds, particularly osmium tetroxide, e.g., to their corresponding glycols.

The patent literature directed to osmium containing hydroxylation catalysts describes various osmium oxides used in conjunction with specific oxidants. The primary oxide catalyst employed in these patents is $OsO_4$, a highly volatile (B.P. 130° C.) and toxic substance. Ordinarily, the toxic nature of $OsO_4$ alone, while troublesome to some extent, could be dealt with by resonably economic precautions. However, the combined properties of high volatility and toxicity human tolerance is 0.002 mg/m$^3$ of air) render this compound extremely dangerous necessitating large capital expenditures in plant safety equipment and design if one attempts to commercialize a process employing this compound as a catalyst. It is for this reason that commercialization of $OsO_4$ based plants has infrequently occurred in the past, if at all. If commercialization is attempted, the aforedescribed capital investment in safety equipment must reduce the profit margin on the products made by these processes.

Accordingly, it would be of extreme economic significance if alternative osmium catalysts could be indentified which possess the property of low volatility and/or low toxicity (in relation to $OsO_4$), together with processes for using the same to achieve glycol product selectivity and yield comparable to or better than the conventional $OsO_4$ catalyst.

Norton, U.S. Pat. No. 3,335,174, is directed to the use of Group Vb, VI-b, and VII metal halides and oxyhalides (e.g., $OsCl_3$) as hydroxylation and esterification catalysts in conjunction with aqueous $H_2O_2$ as an oxidant. However, the process for using this catalyst requires the presence of lower aliphatic hydrocarbon acids such as formic, acetic and propionic acid as solvents. Under these conditions the reaction times vary from ½ to 4 hours, but at the shorter reaction times it is disclosed that substantial amounts of epoxide result thereby indicating that the reaction proceeds via the peracid route wherein epoxide intermediates are hydrolyzed to corresponding diols. When the equivalent of Example 2 of this patent was conducted (see Comparative Example 1 herein) the conversion of hydrogen peroxide was found to be 10%, the selectivity to diol was 10%, the selectivity to diacetate was 20%, and the diol yield was 1%. Clearly, Norton is attempting to utilize the peracid route of olefin oxidations and osmium halide as, in practical effect an intermediate epoxidation catalyst. Unfortunately, however, Norton cannot control the subsequent esterification of epoxide-derived diol and hence more ester forms than diol. Thus, among the major disadvantages of the process described in this patent are the low selectivities to diol, the corrosiveness of metal halides in the presence of glacial acids such as acetic acid, and the use of hydrogen peroxide (an expensive reagent) as the oxidant.

In an extensive review article by Martin Schroder, "Osmium Tetraoxide Cis Hydroxylation of Unsaturated Substrates" Chemical Reviews, Vol. 80, pp. 187-213 (1980) (hereinafter Schroder), the comment is made at page 203 thereof in interpreting Norton that osmium trichloride behaves as a nonvolatile source of osmium tetraoxide in the process of Norton, the tetraoxide being generated in-situ by hydrogen peroxide oxidation. This observation of Schroder, and others (see also Br. Pat. Spec. No. 1,324,763, p.3, col.2, lines 55 et.seq.), is unsupported by experimental data. Moreover, experimental data has been supplied herein to show that osmium-halides are not converted to $OsO_4$ in the presently claimed invention and it is doubted that the same occurs in Norton.

In contrast to the peracid route to olefin hydroxylation and esterification utilized in Norton, it is well known from the technical literature, that olefins can be oxidized directly to their corresponding diols, stoichiometrically or catalytically, with osmium oxide compounds, particularly osmium tetroxide. The direct hydroxylation of olefins is distinctively different from the peracid route of Norton since it does not form an epoxide intermediate.

The non-catalytic, i.e. stoichiometric, cis-hydroxylation of alkenes with $OsO_4$ has been conventionally characterized as taking place via the formation, with the alkene, of an osmium (VI) intermediate ester complex. [See for example, Schroder pp. 187-213.]

To convert the non-catalytically prepared osmium (VI) ester complex intermediate to the diol, the intermediate can be hydrolyzed reductively. Reductive hydrolysis is conventionally carried out by using alkali metal sulfites, bisulfites, lithium aluminum hydride, or hydrogen sulfide to yield the corresponding cis-diols together with lower valence forms of osmium which are removed by filtration.

In contrast to the stoichiometric non-catalytic mode of cis-hydroxylation with $OsO_4$, the catalytic mode employs a secondary oxidant to oxidatively hydrolyze the intermediate Osmium (VI) ester and regenerate the $OsO_4$ which can undergo further reduction by the substrate olefin. A variety of oxidants have been employed in conjunction with the use of $OsO_4$ in the catalytic mode such as $H_2O_2$, t-butyl hydroperoxide and oxygen.

The use of oxygen as oxidant in such osmium oxide based catalytic systems has encountered considerable difficulty due to the appreciable overoxidation of the products, particularly at elevated temperatures (e.g. 70°-80° C.), leading to the formation of keto or acid products. However, if the reaction temperature is lowered to reduce overoxidation, the reaction rate is so low that yields of cis-diol are drastically reduced. An additional disadvantage of the use of oxygen oxidant is that the reaction is pH dependent (See Schroder, page 210, col. 1).

The poor performance of oxygen based osmium catalyzed olefin hydroxylation systems is unfortunate, since such systems have inherent advantages over organic hydroperoxide based systems. For example, hydroxylation systems employing organohydroperoxide oxidants result in the conversion of the organohydroperoxide to its corresponding alcohol during the formation of the desired olefin derived diol. Thus, for example, t-butyl hydroperoxide is converted to t-butyl alcohol. The commercial attractiveness of such processes is dependent on the ability to use or sell the organic alcohol co-product in addition to the diol. Given the fluctuation in economic conditions, however, it may be difficult to dispose of large quantities of these organic alcohol co-products in an economically attractive manner. In any event, it can be troublesome, when the quantity of one product, selected on the basis of marketing possibilities for a given period, necessarily determines the quantity of some other product which may be smaller or larger than desirable in view of changing marketing requirements within that same period. It can, therefore, under certain circumstances be considered as a disadvantage of the aforenoted organohydroperoxide based processes that such large quantities of organic alcohols are formed as co-products, even though under other circumstances the formation of two products may well be found acceptable.

In contrast, oxygen based hydroxylation systems do not produce an oxidant derived alcohol co-product that must be disposed of, which can be a significant advantage.

The search has, therefore, continued for ways of improving the rate and/or selectivity of osmium catalyzed oxygen based processes for hydroxylating olefins.

One step in this direction is disclosed in commonly assigned U.S. patent application Ser. No. 310,097, filed Oct. 9, 1981, by R. Austin and R. Michaelson, the inventors herein. This application describes a process for the hydroxylation of olefins using oxygen as an oxidant, a catalytically active metal oxide catalyst such as OsO4, and at least one transition metal salt co-catalyst such as copper bromide. This process can also be conducted in the optional presence of a second co-catalyst such as alkali metal halides. While the use of the transition metal co-catalyst substantially improves the reaction rate and/or selectivity of the hydroxylation reaction, the search has continued for ways to alleviate the aforedescribed disadvantages of osmium oxides.

Commonly assigned U.S. Pat. No. 4,314,088 issued Feb. 2, 1982 and a continuation-in-part thereof, namely, U.S. patent application Ser. No. 310,099 filed Oct. 9, 1981 by R. Austin and R. Michaelson collectively, disclose the use of various halide containing co-catalysts in conjunction with osmium tetroxide catalyst and organohydroperoxide oxidants to hydroxylate olefins. The halide containing co-catalysts include alkali and alkaline earth metal halides, hydrogen-halides, quarternary hydrocarbyl phosphonium halides, halogens, and transition metal halides. The use of oxygen as an oxidant either alone or in conjunction with a transition metal co-catalyst is not disclosed.

U.S. patent application Ser. No. 399,270 filed July 19, 1982, by R. Austin and R. Michaelson is directed to a process for hydroxylating olefins in the presence of an organohydroperoxide oxidant, an osmium containing catalyst and an organic halogenated hydrocarbon co-catalyst.

Commonly assigned U.S. patent application Ser. No. 394,414, filed July 1, 1982 by R. Michaelson and R. Austin, is directed to the use of carboxylate salts as co-catalysts for use in conjunction with osmium oxides as a catalyst and organohydroperoxide as oxidant to hydroxylate olefins.

Commonly assigned U.S. patent application Ser. No. 397,997 filed July 14, 1982, by R. Michaelson, R. Austin, and D. White is directed to a process for hydroxylating olefins in the presence of a supported osmium containing catalyst (e.g., supported OsBr3), optional co-catalysts and an oxidant selected from hydrogen peroxide, organohydroperoxides and oxygen.

Commonly assigned U.S. patent application Ser. No. 420,137 filed Sept. 20, 1982 by R. Michaelson, R. Austin, and D. White is directed to a process for hydroxylating olefins in the presence of an osmium carbonyl catalyst, optional co-catalysts and an oxidant selected from hydrogen peroxide, organohydroperoxide, and oxygen.

Commonly assigned U.S. patent application Ser. No. 440,964 filed Nov. 12, 1982 by R. Michaelson, R. Austin, and D. White is directed to a process for hydroxylating olefins in the presence of an osmium oxide catalyst, optional co-catalysts and sodium hydroxide as a promoter.

U.S. Pat. No. 2,414,385 discloses the use of hydrogen peroxide and a catalytically active oxide, such as osmium tetroxide, dissolved in an essentially anhydrous, non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically, and disadvantageously, reduce the reaction rate to commercially unacceptable levels. At temperatures greater than 21° C., the formation of aldehydes, ketones, and acids is favored.

U.S. Pat. No. 2,773,101 discloses a method for recovering an osmium containing catalyst such as osmium tetroxide, by converting it to the non-volatile osmium dioxide form, distilling the hydroxylation product, re-oxidizing the osmium dioxide to the volatile osmium tetroxide, and then recovering the same by distillation. Suitable oxidizing agents used to re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other oxidizing agents such as oxygen; perchlorates, nitric acid, chlorine water and the like. As with other methods of the prior art, the above process yields undesirable by-products (See Col. 1, Line 55) thus reducing the selectivity of the process.

British Patent Specification No. 1,028,940 is directed to a process for regenerating osmium tetroxide from reduced osmium tetroxide by treatment of the latter with molecular oxygen in an aqueous alkaline solution. More specifically, it is disclosed that when osmium tetroxide is used by itself as an oxidizing agent, or as a catalyst in conjunction with other oxidizing agents, to oxidize hydrocarbons the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from such compounds as vicinal glycols, olefins, ketones and alcohols.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkylammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as t-butyl hydroperoxide, while a critical pH of 8 to 12 is maintained by a suitable combination of alkali metal buffering compounds. The preparation of propylene glycol utilizing t-butyl hydroperoxide is exemplified in the patent at a selectivity based on the hydroperoxide of 45%.

Japanese Patent Application No. Sho 54-145604, published Nov. 14, 1979, is directed to a process for hydroxylating olefins in the presence of $OsO_4$, a quaternary ammonium salt such as tetraethylammonium bromide, and a peroxide including organoperoxides and $H_2O_2$ as the oxidant.

See also: U.S. Pat. No. 3,317,592 (discloses production of acids and glycols using oxygen as oxidant, $OsO_4$ as catalyst at pH 8 to 10); U.S. Pat. No. 3,488,394 (discloses hydroxylation of olefins by reacting olefin and hypochlorite in the presence of $OsO_4$); U.S. Pat. No. 3,846,478 (discloses reaction of hypochlorite and olefin in an aqueous medium and in the presence of $OsO_4$ catalyst to hydroxylate the olefin); U.S. Pat. No. 3,928,473 (hydroxylation of olefins to glycols with $O_2$ oxidant, octavalent osmium catalyst (e.g. $OsO_4$), and borates as promoter); U.S. Pat. No. 3,931,342 (discloses a process for recovering glycols from an aqueous solution containing alkali metal borate and osmium compounds (e.g. $OsO_4$)); U.S. Pat. No. 3,953,305 (discloses use of $OsO_4$ catalyst for hydroxylating olefins which is regenerated by oxidizing hexavalent osmium with hexavalent chromium and electro-chemically regenerating hexavalent chromium); U.S. Pat. No. 4,203,926 (discloses ethylbenzene hydroperoxide as oxidant used in two-phase system to hydroxylate olefins in presence of $OsO_4$ and cesium, rubidium and potassium hydroxides); U.S. Pat. No. 4,217,291 (discloses the oxidation of Osmium (III) or (IV) in an ionic complex with oxygen and an alkali metal, ammonium, or tetra(lower)alkylammonium cation to a valency of greater than +5 and organohydroperoxides); U.S. Pat. No. 4,299,601 (discloses the use of cesium, rubidium, and potassium hydroxides as promoters for $OsO_4$ catalyst and t-butyl hydroperoxide oxidant for hydroxylating olefins); U.S. Pat. No. 4,280,924 (discloses a process for regenerating perosmate catalyst, e.g., cesium, rubidium and potassium perosmate); and European Patent Application No. 0004725 (discloses production of glycols from olefins using Cu or Fe ions, and ions of Br and I, and $O_2$, but in the absence of osmium.

None of the aforenoted patents disclose the use of osmium halides or oxy halides as catalysts for cis-hydroxylation reaction between olefins, and oxygen oxidants.

Accordingly, the search has continued for relatively non-volatile and/or relatively non-toxic osmium compounds capable of catalyzing such hydroxylation reactions between olefins and oxygen. The present invention is a result of this search.

SUMMARY OF THE INVENTION

In one aspect of the present invention there is provided a process for hydroxylating at least one olefinic compound having at least one ethylenic unsaturation which comprises reacting said olefinic compound in admixture with water, a molecular oxygen containing oxidant, and a catalyst composition comprising (i) at least one catalyst (a) being capable of catalyzing said hydroxylation reaction, and (b) being initially added to said admixture as at least one osmium-halide; and (ii) a co-catalyst comprising at least one transition metal, said transition metal being selected from the group consisting of Fe, Co, Ni, Cu, V, Mn, Sc, Ti, Mo, Ru, Rh, Pd, and W; said reaction being conducted in a manner and under conditions sufficient to convert at least one of said ethylenic unsaturation to its corresponding diol.

DESCRIPTION OF PREFERRED EMBODIMENTS

In accordance with the present invention, at least one olefin containing at least one ethylenic unsaturation is reacted with oxygen, in the presence of water, at least one catalyst, and at least one transition metal containing co-catalyst, under conditions and in a manner sufficient to directly hydroxylate at least one of said ethylenically unsaturated groups to its corresponding diol group.

The catalysts employed in the process of the present invention comprise compounds containing osmium and halogen. Such osmium-halogen containing compounds include osmium halides and osmium oxy halides, and complexes thereof, (all of the above being referred to herein collectively as osmium-halides) such as those represented by the structural formulae: $Os(X)_n$ (e.g., $OsX_3$, $OsX_4$, and $OsX_5$); $Os(OH)X_3$; $OsOX_4$; $OsOX_5N$; $OsO_3X_2$; $OsONX_4$; $(M)_n'[OsX_6]^{-2}$; $(M)_n'[OsO_2X_4]^{-2}$; $M^{+1}[Os(OH)X_5]^{-1}$; $(M)_n'[OsO_4X_2]^{-2}$; $(M)_n'[OsO_2(OH)_2X_2]^{-2}$; $(M)_n'[OsNX_5]^{-2}$; and mixtures thereof: wherein X is halogen independently selected from the group consisting of F, Cl, Br and I; n is an integer which can vary from 3 to 5, M is a cation including cations of alkali (e.g., Li, Na, K, Rb, Cs, Fr) metals, alkaline earth metals (e.g., Be, Mg, Ca, Sr, Ba, Ra), ammonium (i.e. $NH_{4+}$), tetrahydrocarbyl ammonium (e.g. $(R)_4N^+$) and tetrahydrocarbyl phosphonium (e.g. $(R)_4P^+$) said tetrahydrocarbyl groups being as defined in connection with Group 5 co-catalysts discussed below; and n' is a number which is selected in conjunction with the valence of cation M to achieve a neutral complex; preferably n' is 1. The identity of the osmium-halide is typically selected such that it is at least partially soluble, preferably completely soluble in the reaction mixture employed.

Representatives examples of such compounds include $OsF_3$, $OsCl_3$, $OsBr_3$, $OsI_3$, $OsF_4$, $OsCl_4$, $OsBr_4$, $OsI_4$, $OsF_5$, $Os(OH)Cl_3$, $Os(OH)F_3$, $OsOF_4$, $OsOCl_4$, $OsO_3F_2$, $OsONCl_4$, $K_2[OsCl_2Br_2I_2]$, $(NH_4)_2[OsF_6]$, $Ca[OsI_6]$, $Li_2[OsO_2Cl_4]$, $(CH_3CH_2)_4N[Os(OH)Cl_5]$, $(CH_3CH_2)_4P[Os(OH)Br_5]$, $Mg[OsO_4F_2]$, $Na_2[OsO_2(OH)_2Cl_2]$, $Ba[OsCl_5N]$, $K_2[OsNCl_5]$, $K_2[OsNBr_5]$, and mixtures thereof.

The preferred catalysts are those having a boiling point at atmospheric pressure of typically greater than about 130° C., preferably greater than about 150° C., and most preferably greater than about 175° C.

The most preferred catalysts are those represented by the structural formula $OsX_3$ wherein the order of preference of the halogen constituting X is Br, Cl, I, and F.

Since the volatility of these osmium catalysts is reduced, preferably substantially, relative to $OsO_4$, the expensive equipment necessary to deal with the volatile and toxic nature of $OsO_4$ can be eliminated or reduced substantially in cost thereby rendering the overall process extremely competitive from an economic standpoint.

The catalysts having the formula $Os(X)_n$ can be prepared by the general methods described in "Advanced Inorganic Chemistry" by Cotton and Wilkinson (hereinafter Cotton and Wilkinson), p. 909 (4th ed. 1980).

Catalysts having the formula $OsOX_4$ and $OsO_3X_2$ can be prepared by the method described in the "J. Inorganic Nuclear Chemistry" by Hepworth and Robinson, Vol. 4, p.24 (1957).

Catalysts having the formula $Os(OH)X_3$ can be prepared by the method described in "Comprehensive Inorganic Chemistry", Trotman-Dickerson (ed.) Vol. 3, p. 1217 (1973).

Catalysts having the formula $OsONX_4$ can be prepared by the method described in "Comprehensive Inorganic Chemistry" described above at Vol. 3, p. 1233.

Catalysts having the formula $(M)_n'[OsX_6]^{-2}$ can be prepared by the general method described in Cotton and Wilkinson, p. 919.

Catalysts having the formula $(M)_n'[OsO_2X_4]^{-2}$ can be prepared by the general method described in Cotton and Wilkinson, p. 917.

Catalysts having the formula $M^{+1}[Os(OH)X_5]^{-1}$ can be prepared by the general method described in "Z. Anorg. Allgen. Chem." by Krauss and Wilken (hereinafter Krauss and Wilken) Vol. 137, p. 349 (1924).

Catalysts having the formula $(M)_n'[OsO_4X_2]^{-2}$ can be prepared by the method described in Krauss and Wilken, Vol. 145, p. 151 (1925).

Catalysts having the formula $(M)_n'[OsO_2(OH)_2X_2]^{-2}$ can be prepared by the method described in Cotton and Wilkinson, p. 914.

Catalysts having the formula $(M)_n'[OsNX_5]^{-2}$ can be prepared by the method described in "Inorganic Synthesis", by E. G. Rochow, Vol. 6, p. 204 (1960).

The disclosures of all of the above references illustrating the methods of preparation of the aforenoted osmium-halide catalysts are herein incorporated by reference.

The osmium-halide catalysts are employed in amounts effective to catalyze the hydroxylation reaction. Thus, while any effective amount of catalyst will suffice, it is preferred that such effective amounts constitute typically from about $1\times10^{-1}$ to about $1\times10^{-8}$ moles, preferably from about $1\times10^{-2}$ to about $1\times10^{-6}$ moles, and most preferably from about $1\times10^{-2}$ to about $1\times10^{-4}$ moles, of osmium in the osmium-halide catalyst per mole of olefin ethylenic unsaturation to be hydroxylated.

Alternatively, such amounts may be expressed as varying from about 1 to about 10,000, preferably from about 50 to about 1,000, and most preferably from about 200 to about 800 ppm, based on the total weight of liquid reaction medium.

The osmium-halide catalysts are soluble in aqueous and/or organic polar solvent systems described hereinafter and can be dissolved in said systems for addition to the reaction vessel. For example, the osmium-halide catalysts are preferably added to the reaction vessel as a solution having the catalyst dissolved in a water/organic solvent mixture.

The afore-described osmium-halide catalysts are employed in combination with at least one of the transition metal containing co-catalysts described hereinafter (e.g. see Group 6 co-catalysts), and optionally with one or more additional promoters (also referred to herein as co-catalysts), which increase the selectivity and/or reaction rate of the hydroxylation reaction.

For example, suitable promoters or co-catalysts include alkali (e.g., Li, Na, K, Rb, Cs, and Fr), and alkaline earth metal (e.g. Be, Mg, Ca, Sr, Ba and Ra); halides, hydroxides, carboxylates, aryloates, aryolates and pseudo halides; tetrahydrocarbyl ammonium: hydroxides, halides, carboxylates, aryloates, and aryolates; tetrahydrocarbyl phosphonium: hydroxide, halides, carboxylates, aryloates, aryolates; transition metal containing compounds including transition metal: halide, porphyrins, carboxylates, and aryloates; hydrogen halides; alkyl, aryl, aralkyl, and alkaryl halides; Group III-b, (i.e., B, AL, Ga, In, Tl), IV-b (i.e., Si, Ge, Sn, Pb), V-b (i.e., N, P, As, Sb, Bi) and VI-b (i.e., S, Se, Te, Po) halides; and the halogens $F_2$, $Cl_2$, $I_2$, $Br_2$.

More specifically, suitable alkali and alkaline earth metal halide co-catalysts (referred to herein as Group 1 co-catalysts) include the Li, Na, K, Rb, and Cs iodides, bromides, chlorides and fluorides; and Mg, Ca, Sr, and Ba, iodides, bromides, chlorides, and fluorides and mixtures thereof. Preferred Group 1 co-catalysts include the Na, K, Rb, Cs, Mg and Ca halides.

Suitable alkali and alkaline earth metal hydroxide co-catalysts (referred to herein as Group 2 co-catalysts) include LiOH, NaOH, KOH, RbOH, CsOH, $Ca(OH)_2$, $Ba(OH)_2$, $Mg(OH)_2$ and mixtures thereof.

Preferred Group 2 co-catalysts include the Na, K, Rb, Mg, and Ca hydroxides.

Suitable alkali and alkaline earth metal: carboxylate, aryloate, and aryolate co-catalysts (referred to herein as Group 3 co-catalysts) include those which possess as anions respectively:

(a) carboxylate anions represented by the structural formula:

$$(R_1)\!\!\!\!-\!\!\!C\!\!-\!\!O^-  \qquad (I)$$
$$\phantom{(R_1)\!-}\overset{\displaystyle O}{\|}$$

wherein $R_1$ can be substituted or unsubstituted: alkyl, typically alkyl of from about 1 to about 10 carbons, preferably about 1 to about 5 carbons, and most preferably about 1 to about 3 carbons, or aralkyl, typically aralkyl wherein the aryl group thereof is as defined in connection with Ar of structural formula II below and the alkyl group thereof is as defined immediately above; said $R_1$ substituents including: hydroxyl; halide (i.e., F, Cl, Br, and I); ether groups represented by the structural formulae $-O-R_2$ and $-R_3-O-R_2$ wherein $R_2$ and $R_3$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and ester groups represented by the structural formulae:

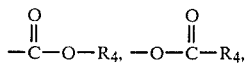

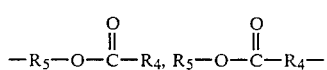

wherein $R_4$ and $R_5$ which may be the same or different are as defined in connection with $R_2$ and $R_3$; and mixtures thereof;

(b) aryloate anions represented by the structural formula:

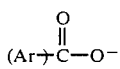 (II)

wherein Ar is selected from the group consisting of substituted and unsubstituted: aryl, typically aryl of from about 6 to about 14 carbons, preferably from about 6 to about 10 carbons (e.g., 6 carbons), and alkaryl, typically alkaryl wherein the alkyl group contains from about 1 to about 6 carbons, preferably from about 1 to about 3 carbons, and the aryl group thereof is as defined above, and wherein said substituents on the Ar group are as defined above in connection with $R_1$; and (c) aryolate anions represented by the structural formula:

 (III)

wherein Ar is as described above in connection with the structural formula II, and preferably is aryl.

Illustrative examples of such Group 3 co-catalysts include: sodium acetate, potassium acetate, calcium, acetate, cesium acetate, magnesium acetate, potassium ethanoate, sodium propanoate, magnesium butanoate, strontium pentanoate, sodium benzoate, potassium benzoate, magnesium benzoate, calcium benzoate, sodium naphthoate, potassium naphthoate, beryllium naphthoate, sodium 4-(6-methyl-2-naphthyl)-pentanoate, potassium 3-(7-methyl-1-naphthyl)-propanoate, magnesium 2-(4-propyl-1-benzyl)-ethanoate, calcium phenolate, sodium naphtholate, potassium naphtholate, sodium 3-(ethoxy)-propanoate, potassium 4-(propoxycarbonyl)-butanoate, calcium 3-(propylcarbonyloxy)-propanoate, magnesium 2-(methylcarbonyloxymethyl)-acetate, beryllium 4-(ethoxycarbonylmethyl)-butanoate, cesium 4-(ethoxymethyl)-benzoate, sodium 3-(propoxy)-naphthoate, potassium 4-(ethoxycarboyl)-benzoate, barium 2-(hydroxy)-acetate, rubidium 2-chloropanoate, magnesium 4-bromobenzoate, magnesium phenolate, and mixtures thereof.

Preferred Group 3 co-catalysts include the Na, K, Rb and Cs acetates.

Suitable alkali and alkaline earth metal pseudo halide co-catalysts (referred to herein as Group 4 co-catalysts) include those which possess pseudo halide anions selected from the group consisting of: $SCN^-$, $SeCN^-$, $TeCN^-$, $OCN^-$, and $CON^-$, and mixtures thereof.

Illustrative examples of such Group 4 co-catalysts include NaSCN, NaSeCN, KSeCN, CsSeCN, NaTeCN, KTeCN, NaOCN, NaCNO, KOCN, KCNO, CsOCN, CsCNO, CsTeCN, $Mg(SeCN)_2$, $Ca(TeCN)_2$, $Ca(OCN)_2$, $Ca(CNO)_2$.

Preferred Group 4 co-catalysts include the Na, K, Rb and Cs thiocyanates.

Tetrahydrocarbyl ammonium or phosphonium salt co-catalysts (referred to herein as Group 5 co-catalysts) possess a cation and an anion. The representive cations can be represented by the respective structural formula $(R)_4N^+$ and $(R)_4P^+$ wherein R is a hydrocarbyl group independently selected from the group consisting of substituted and unsubstituted: alkyl, typically allkyl having from about 1 to about 30 carbons, preferably from about 1 to about 20 carbons, and most preferably from about 1 to about 10 (e.g. 1–5) carbons, aryl, preferably aryl having from 6 to about 14 carbons, and most preferably from 6 to about 10 carbons, and alkaryl and aralkyl wherein the aryl and alkyl groups thereof are as described immediately above; said R substituents being as defined in connection with the substituents of $R_1$ described above. Accordingly, the term hydrocarbyl is intended to include both substituted and unsubstituted groups, and mixtures thereof. The anion of the Group 5 co-catalysts are selected from the group consisting of hydroxyl, halide, pseudo halide, carboxylate, aryloate and aryolate, said pseudo halide, carboxylate, aryloate, and aryolate anions, being as defined above in connection with the anions of the alkali and alkali metal salt co-catalysts described above.

Illustrative examples of such Group 5 co-catalysts include tetramethylammonium bromide, tetraethylphosphonium chloride, tetradecylphosphonium bromide, tetraphenylammonium chloride, tetraphenylphosphonium bromide, dimethyldiethylammonium iodide, methyltriethylphosphonium chloride, tetrabutylammonium chloride, phenyltrimethylammonium bromide, phenyltrimethylphosphonium chloride, phenyltriethylammonium iodide, phenyltriethylphosphonium chloride, tetraethylammonium hydroxide, tetrabutylammonium hydroxide, tetraethylphosphonium hydroxide, phenyltriethylammonium hydroxide, phenyltrimethylphosphonium hydroxide, tetraethylammonium acetate, tetrabutylphosphonium acetate, phenyltriethylammonium acetate, phenyltrimethylphosphonium acetate, tetraethylammoniumbenzonate, phenyltrimethylphosphonium benzoate, phenyltriethylammonium naphthoate, tetraethylammonium phenolate, tetrabutylphosphonium naphtholate, tetra-2-(methoxy)-ethylphosphonium chloride, tetra-4-(propoxymethyl)phenylammonium bromide, di-3-(methoxycarbonyl)-propyl-diethylphosphonium idodide, di-4-(ethylcarbonyloxy)-butyl-dimethylammonium chloride, tetra-5-(ethoxycarbonylmethyl)-pentylphosphonium bromide, tetra-4-hydroxybutylammonium acetate, tetra-3-chloropropylphosphonium acetate, tetramethylammonium thiocyanate, tetraethylphosphonium-seleniocyanate, tetra-(4-methylphenyl)-ammonium chloride, tetra-(3-phenyl-1-propyl)-phosphonium bromide.

Preferred Group 5 co-catalysts include the unsubstituted tetra lower alkyl (e.g., $C_1$ to $C_5$ alkyl) ammonium hydroxides, iodides, bromides, fluorides, chlorides and acetates.

Transition metal containing co-catalysts (referred to herein as Group 6 co-catalysts) include those wherein the transition metal is selected from the group consisting of Fe, Co, Ni, Cu, V, Cr, Mn, Sc, Ti, Mo, Ru, Rh, Pd, and W, preferably Cu, Fe, Ni, Co and Mn, and most preferably Cu, and mixtures thereof. Accordingly, the Group 6 co-catalyst is typically employed as a transition metal salt having a transition metal cation and an anion.

Anions of the Group 6 co-catalysts include halide, porphyrin (as defined in the Condensed Chemical Dictionary 9th ed. revised by G. Hawley (1977) including benzoporphyrins), pseudo halide, carboxylate and aryloate; said psuedo halide, carboxylate and aryloate anions being as defined generally in connection with the alkali and alkaline earth metal containing co-catalysts and as illustrated by specific examples of suitable anions in conjunction with other co-catalysts described herein.

Representative examples of Group 6 co-catalysts include $FeF_3$, $FeCl_3$, $FeBr_3$, $FeF_2$, $FeCl_2$, $FeBr_2$, $FeI_2$, $CoCl_2$, $CoF_3$, $CoF_2$, $NiF_2$, $NiBr_2$, $NiI_2$, $NiCl_2$, $CuF_2$, $CrBr_2$, $CuI_2$, $CuCl_2$, $CuI$, $CuCl$, $CuBr$, $VF_5$, $VF_4$, $VF_3$, $VF_2$, $VCl_4$, $VCl_3$, $VBr_4$, $VBr_3$, $VI_3$, $CrF_2$, $CrF_3$, $CrF_4$, $CrF_5$, $CrF_6$, $CrCl_3$, $CrCl_4$, $CrBr_3$, $CrBr_4$, $CrI_3$, $MnCl_2$, $MnCl_3$, $MnCl_4$, $MnBr_3$, $MnI_3$, $ScCl_3$, $ScBr_3$, $ScF_3$, $TiCl_4$, $TiBr_4$, $TiF_4$, $MoCl_3$, $Mo_2Cl_{10}$, $MoBr_4$, $Mo_2F_9$, $MoF_6$, $MoF_5$, $RuF_5$, $RuF_3$, $RuF_4$, $RuF_6$, $RuCl_3$, $RuCl_4$, $RuCl_6$, $RuBr_6$, $RhF_3$, $RhF_4$, $RhF_6$, $PdF_2$, $PdCl_2$, $PdBr_2$, $PdI_2WCl_6$, $WBr_5$, $WCl_3$, $WBr_3$, $WI_3$, copper acetate, copper naphthoate, copper benzoate, copper propanoate, iron acetate, iron benzoate, iron naphthoate, copper 4-ethyl benzonate, iron 4-butylbenzoate, nickel acetate, nickel benzoate, nickel naphthoate, copper decanoate, iron hexanoate, iron phthalocyanine, manganese phthalocyanine, copper phthalocyanine, nickel phthalocyanine, and the Fe, Mn, Cu, and Ni porphyrin salts.

Preferred Group 6 co-catalysts include copper bromide, chloride, iodide, and acetate; iron bromide, chloride, iodide and acetate; manganese bromide, chloride, and acetate, and mixtures thereof.

Suitable hydrogen halides (referred to herein as Group 7 co-catalysts) include HF, HCL, HBr and HI.

Preferred Group 7 co-catalysts include HI, HBr, and HCl.

Suitable alkyl, aryl, aralkyl and alkaryl halide co-catalysts (referred to herein as Group 8 co-catalysts) include those represented by the respective structural formulae:

$$(R'-(X)_{n''} \quad \quad (IV)$$

and

$$(Ar'-(X)_{n''} \quad \quad (V)$$

wherein R' can be substituted or unsubstituted: alkyl, typically alkyl of from about 1 to about 20, preferably from about 1 to about 10, most preferably from about 1 to about 5 carbons, and aralkyl, typically aralkyl wherein the alkyl group thereof is as defined immediately above and the aryl group thereof is as defined in connection with Ar' below; Ar' is aryl, typically aryl of from about 6 to about 14, preferably 6 to about 10, most preferably 6 carbons, and alkaryl wherein the alkyl and aryl groups thereof are as defined immediately above; X is at least one halogen independently selected from the group consisting of F, CL, Br and I, and preferably I and Br; n'' is an integer of from about 1 to about 10, preferably from about 2 to about 8, and most preferably from about 2 to about 6; and said R' substituents include hydroxyl.

Representative Examples of Group 8 co-catalysts include iodomethane, bromomethane, iodoethane, bromoethane, 1,2-dibromoethane, chloroethane, 1,2-dichloroethane, 1-iodopropane, 1-bromopropane, 1-chloropropane, 1-iodo-1-methylethane, 2-bromo-1-methylethane, 2-chloro-1-methylethane, 1-iodobutane, 2-bromobutane, 1-chlorobutane, 1-iodo-1-methylpropane, 1-bromo-1-methylpropane, 1-chloro-1-methylpropane, 1-iodo-1,1-dimethylethane, 1-chloro-1, 1-dimethylethane, 1-bromo-1,1-dimethylethane, phenyliodomethane, phenylchloromethane, phenylbromomethane, 1,2-dichlorobenzene, 2-bromoethanol, 2-chloroethanol, 2-iodoethanol, 1-phenyl-2-iodoethane, 1-phenyl-4,4-dichlorobutane, 1-(1,2-dichloroethyl)-benzene, 1-(1-chloropropyl)-naphthalene, t-butyl bromide, t-butyl iodide, and mixtures thereof.

Preferred Group 8 co-catalysts include bromomethane, 1-bromobutane, 1-iodobutane, 1-bromo-1,1-dimethylethane, 1-iodo-1,1-dimethylethane, 2-bromoethanol, and 2-chloroethanol.

Representative examples of suitable Group III-b, IV-b, V-b and VI-b metal halides (according to the periodic chart of Cotton and Wilkinson "Advanced Inorganic Chemistry" [3rd ed. 1972]) referred to herein as Group 9 co-catalysts include halides of Al, Ga, In, Tl, Ge, Sn, Pb, P, Si, As, Sb, Bi, S, Se, Te, and Po.

Specific Group 9 metal halides include $AlCl_3$, $GaBr_3$, $TlCl_3$, $SiCl_4$, $SiBr_4$, $PI_3$, $PBr_3$, $SbF_5$, $SbBr_3$, $SbI_3$, $BiCl_3$, $BiBr_3$, $AsI_3$, $AsBr_3$, $AsCl_3$, $SeF_4$, $SeCl_4$, $SeBr_4$, $TeF_4$, and mixtures thereof.

Suitable halogen co-catalysts (referred to herein as Group 10 co-catalysts) include $F_2$, $Cl_2$, $Br_2$, and $I_2$.

In addition to the Group 6 co-catalysts, one or more of the remaining optical co-catalysts described in each of the aforenoted groups can be employed alone or in conjunction with one or more co-catalysts in the same group and/or with one or more of the co-catalysts in the remainder of said groups in any amounts effective to increase the rate and/or selectivity of the hydroxylation reaction relative to the rate observed in their absence.

Accordingly, while any effective amount of co-catalyst can be employed, it is contemplated that such effective amounts constitute typically from about 1 to about 10,000 mole percent, preferably from about 50 to about 1,000 mole percent, and most preferably from about 200 to about 500 mole percent, Group 1 co-catalyst based on the total number of moles of osmium in the osmium-halide catalyst employed; typically from about 1 to about 10,000 mole percent, preferably from about 50 to about 1,000 mole percent, and most preferably from about 200 to about 500 mole percent, Group 2 co-catalyst based on the total number of moles of the osmium in the osmium-halide catalyst employed; typically from about 1 to about 10,000 mole percent, preferably from about 50 to about 1,000 mole percent, most preferably from about 200 to about 500 mole percent, Group 3 co-catalyst, based on the total number of moles of osmium in the osmium-halide catalyst employed; typically from about 1 to about 10,000 mole percent, preferably from about 50 to about 1,000 mole percent, and most perferably from about 200 to about 500 mole percent, Group 4 co-catalyst, based on the total number of moles of osmium in the osmium-halide catalyst employed; typically from about 1 to about 10,000 mole percent, preferably from about 50 to about 1,000 mole percent, and most preferably from about 200 to about 500 mole percent, Group 5 co-catalyst based on the total number of moles of osmium in the osmium-halide catalyst employed; typically from about 1 to about 10,000 mole percent, preferably from about 50 to about 1,000 mole percent, and most preferably from about 200 to about 500 mole percent, Group 6 co-catalyst based on the total number of moles of osmium in the osmium-halide catalyst employed, typically from about 1 to about 10,000 mole percent, preferably from about 50 to about 1,000 mole percent, and most preferably from about 200 to about 500 mole percent, Group 7 cocatalyst based on the total number of moles of osmium in the osmium-halide catalyst employed, typically from about 1 to about 10,000 mole percent, preferably from about 50 to about 1,000 mole percent, and most preferably from about 200 to about 500 mole percent, Group 8 co-catalyst based on the total number of moles of osmium in the osmium-halide catalyst employed; typically from about 1 to about 10,000 mole percent, preferably from about 50 to about 1,000 mole percent, and most preferably from about 200 to about 500 mole percent, Group 9 co-catalyst based on the total number of moles of the osmium in the osmium-halide catalyst employed; and typically from about 1 to about 10,000 mole percent, preferably from about 50 to about 1,000 mole percent, and most preferably from about 200 to about 500 mole percent, Group 10 co-catalyst based on the total number of moles of the osmium in the osmium-halide catalyst.

The aforedescribed catalyst composition comprising at least two components, namely, a catalytically active osmium-halide, and at least one of said transition metal containing co-catalyst unexpectedly substantially improves the rate of reaction for hydroxylating olefins with molecular oxygen relative to conventional catalyst systems. Although the exact mechanism and reason for this effect is not fully understood, it is considered that the results speak positively for themselves. However, the following is offered as an explanation of the mechanism for the observed catalytic effect in connection with the use of said catalyst composition although such explanation is not intended to be exhaustive of all possible mechanistic details. The osmium-halide is believed to add across the olefin double bond of the compound to be hydroxylated to yield an intermediate cis-ester complex. The osmium in this cis-ester complex is reduced thereby necessitating reoxidation of the osmium for further catalytic activity. The glycol product is then believed to be obtained from this complex by oxidative hydrolysis in the presence of oxygen. However, it is further believed that the transition metal co-catalyst serves to mediate the reoxidation of osmium by oxygen upon hydrolysis of the glycolate, the transition metal itself being reduced in the process.

Furthermore, the presence of a halo-moiety in the reaction mixture is believed to facilitate the rate of hydrolysis of the glycolate intermediate and may also help to mediate the reoxidation of the transition metal.

More specifically, by "halo-" is meant to include halogen in the form of organic and inorganic halide salts or complexes, halogenated hydrocarbons, hydrogen halides as well as the free halogens themselves. Accordingly, it is preferred to provide a halo-source in the reaction mixture in addition to the halogen of the osmium-halide. This is typically achieved through the use of a transition metal halide as the co-catalyst. If, however, the source of the transition metal containing co-catalyst is not a halide salt, it is preferred to introduce the additional halo-source through an alternative means. This can easily be achieved through the appropriate selection of any halo-containing Group 1 to 5 and 6 to 10 co-catalysts, such as for example those described hereinabove including alkali or alkaline earth metal halides, tetrahydrocarbyl ammonium or phosphonium halides, hydrogen halides, halogenated hydrocarbons, metal halides and halogens. The halogen in the osmium-halide in addition to rendering the osmium catalyst less volatile and/or toxic than $OsO_4$, is also believed to contribute to rate enhancement as a halo-source of the overall reaction in the reaction system described herein. For economic reasons it may be more desirable to employ an inexpensive halo-source such as NaBr to fulfill the aforedescribed halogen balance rather than use the more expensive transition metal halides for this purpose.

Thus, for optimum performance of the reaction system, it is preferred to establish a balance, in terms of amounts, between osmium in the osmium-halide, the transition metal of the co-catalyst, and halogen in the halo-source present in the reaction mixture. Accordingly, it is contemplated that the mole ratio of Os:transition metal:halogen in the halo-source in contact with the olefin to be hydroxylated be controlled to be typically from about 1:1:1 to about 1:100:1000, preferably from about 1:10:100 to about 1:50:500, and most preferably from about 1:15:20 to about 1:40:200. In satisfying this balance any halogen in the halo-source, e.g. the osmium-halide catalyst, or co-catalysts is taken into consideration.

Furthermore, in view of the above discussion, it is recommended for best results that the most preferred valence of the transition metal of the co-catalyst as initially employed be that which represents the highest stable oxidation state thereof, since such metals must be capable of being reduced upon oxidizing the osmium. While this is not critical, it avoids the need in some instances to initially oxidize the transition metal in-situ so that it can be reduced.

Illustrative examples of suitable co-catalyst combinations include $CuBr_2$ and NaCl; $CuCl_2$ and $NaBr_2$; $FeCl_3$ and NaCl; $CuBr_2$ and tetraethylammonium chloride; $FeCl_2$ and KBr; $FeBr_3$ and CsCl; and CuI and NaBr.

The oxidant is molecular oxygen which can be employed as pure oxygen or an oxygen containing gaseous mixture (e.g. containing one or more inert gases such as $CO_2$, $N_2$ or air). Generally, the oxygen is present within, preferably dissolved in, the reaction mixture in amounts sufficient to achieve hydroxylation of the olefin.

Thus, the molar ratio of oxygen to olefin ethylenic unsaturation can vary widely but for safety reasons it is typically maintained outside explosive limits, said explosive limits usually being expressed as weight percent ratios.

For example, when hydroxylating ethylene or propylene, if oxygen is in excess, the ratio typically will be about 98 weight percent oxygen or more and 2 percent or less of the olefin based on the total weight of these two reactants. Alternatively, if the olefin is in large excess, the oxygen concentration typically will be about 10 weight percent and about 90 weight percent olefin. When oxygen is in excess, olefin can be added during the reaction as the reaction proceeds. On the other hand, where the olefin is in excess, oxygen can be added during the reaction as the oxygen is consumed.

Accordingly, in view of the above, oxygen preferably is dissolved in the reaction mixture in an amount sufficient to achieve a molar ratio of ethylenic unsaturation to be hydroxylated in the olefin to oxygen in excess of 1:1 typically up to as high as 100:1; and outside the explosive limits of the reaction mixture. It will be understood that when either olefin or $O_2$ is employed in substantial excess of stoichiometry for safety reasons, the conversion in a batch process will necessarily be very low if based on the component present in large excess. This is not a problem in a continuous process since unreacted components are recycled.

It is also critical to have water present during the hydroxylation reaction since the water is believed to contribute one of the oxygen molecules constituting one of the hydroxyl groups in the resulting glycol. The source of this water is not critical. Thus, any water formed in-situ during the reaction can contribute to the water content for the reaction. Water can also be added separately. Consequently, water is provided to, and/or is present, in the initial reaction mixture in at least a stoichiometric molar ratio with the molar amount of ethylenic unsaturation of the olefin to be hydroxylated. Such ratios preferably also are present in the reaction mixture at any given time after start-up. Accordingly, water is present in the reaction mixture at molar ratios of water to olefin ethylenic unsaturation to be hydroxylated in the reaction mixture of from about 1:1 to about 100:1, preferably from about 1:1 to about 50:1, and most preferably from about 1:1 to about 20:1. Such molar ratios typically can be achieved by controlling the amount of water in the reaction mixture (including water formed in-situ) to be from about 1 to about 90 percent, preferably from about 15 to about 85 percent, and most preferably from about 20 to about 60 percent, by weight, based on the total weight of the reaction mixture. Preferably the amount of water employed is less than that which will cause separation of the reaction mixture into an aqueous phase and organic phase although this is not a critical condition.

The amount of water employed within the aforedescribed ranges is preferably also related to the amount of $O_2$ in the system. Thus, the mole ratio of $H_2O$ to $O_2$ dissolved in the reaction mixture is typically controlled to be from about 1:1 to about 30:1, preferably from about 1:1 to about 15:1, and most preferably from about 1:1 to about 6:1.

Olefins which can be hydroxylated in accordance with the present invention contain at least one ethylenic unsaturation and comprise any of the unsaturated aliphatic or alicyclic compounds well known in the art for undergoing such hydroxylation reactions. Typically, such compounds will contain from about 2 to about 20 carbons, preferably from about 2 to about 10 carbons, and most preferably from about 2 to about 5 carbons. Such compounds may be straight or branched chain, mono-olefinic, di-olefinic, or poly-olefinic, conjugated or non-conjugated. They may be substituted with such groups are aryl, preferably aryl of from about 6 to about 14 carbons, alkyl, preferably alkyl of from 1 to 10 carbons, or aralkyl or alkaryl wherein the alkyl and aryl portions thereof are as described above, as well as with functional groups such as hydroxyl, carboxyl and anhydride.

Typical of such olefins are those represented by the structural formula:

(VI)

wherein $R_6$, $R_7$, $R_8$, and $R_9$, which may be the same or different, are selected from the group consisting of hydrogen; substituted or unsubstituted: alkyl, aryl, alkaryl, and aralkyl hyrocarbyl groups, said hydrocarbyl groups being preferably as defined immediately above; or any two of said $R_{6-9}$ groups together can constitute a cycloalkyl group typically of from about 4 to about 12, preferably from about 5 to about 8 carbons.

Representative olefins which can be hydroxylated and contain at least one ethylenic unsaturation include: ethylene, propylene, butene-1, butene-2, isobutene, pentene-1, pentene-2, butadiene, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylclyclohexene, isopropylcyclohexene, butylcyclohexene, octylcyclohexene, dodecyclohexene, arcolein, 1,2,3,4-tetrahydrophthalic anhydride, methyl methacrylate, styrene, cholestrol, acrylic acid and mixtures thereof.

The preferred olefins are ethylene, propylene, isobutylene, butadiene, styrene, allyl alcohol and allyl chloride.

The most preferred olefin is ethylene and/or propylene.

The preferred mode for conducting the hydroxylation reaction is in a liquid reaction mixture, preferably provided as a homogeneous or substantially homogeneous medium and preferably but optionally by using an inert organic solvent to dissolve or assist in dissolving the osmium-halide containing catalyst, co-catalysts, and reactants.

Partial immiscibility of the solvent with water is acceptable although not preferred. By an inert solvent is meant one which does not undergo oxidation during the course of the reaction.

Suitable inert organic solvents preferably possess polar functional groups and include aliphatic or aromatic alcohols having from 1 to about 10 carbon atoms, preferably tertiary alcohols, aliphatic or aromatic ketones having from 3 to about 10 carbon atoms, aliphatic or alicyclic ethers having from 2 to about 10 carbon atoms, glycols having from 2 to about 10 carbon atoms, N,N-dialkylamides having from 3 to about b 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimethyl formamide, diethylformamide, dimethylacetamide, dimethylsulfoxide, diethylsulfoxide, di-n-butyl sulfoxide, diphenylsulfoxide, dibenzylsulfoxide, dimethylsulfone, diethylsulfone, tetramethylenesulfone, diphenyl sulfone, acetonitrile, pyridine, dioxane, tetrahydrofuran, tetrahydropyran, dioxolane, and mixtures thereof.

The preferred solvents include those which are substantially or completely miscible with water such as t-butyl alcohol, methanol, as well as glycols and/or polyols derived from the olefin being hydroxylated.

The most preferred solvents are dipolar an aprotic such as sulfolane, acetonitrile, N,N-dimethylacetamide, and N,N-dimethylformamide.

The inert solvent is preferably employed in amounts sufficient to achieve a homogeneous solution with respect to at least the olefin and catalyst system. Typically, such amounts can vary from about 0 to about 90 (e.g. 70 to 90) percent, preferably from about 20 to about 80 percent, and most preferably from about 20 to about 50 percent, by weight, based on the total weight of the reaction mixture.

The pH of the reaction mixture initially and/or during the hydroxylation reaction need not be rigidly controlled although it will typically not be allowed to drop below about 4, preferably not below about 6. Likewise, the pH of the reaction mixture preferably will not be allowed to exceed about 12 although the process can still be conducted at a pH below 4 and about 12. Generally, the pH of the reaction mixture typically will autogeneously vary, or can be maintained by the use of buffers, between about 4 and 12, preferably between about 4 and about 10, (e.g. about 5 to about 10) and most preferably between about 4 and about 8 (e.g. about 5 to about 8).

It is an advantage of the present invention that the oxygen based reaction system described herein is not extremely pH dependent, unlike conventional oxygen based hydroxylation systems. For example, some HBr may form from some of the $OsBr_3$ catalyst employed under reaction conditions. Such in-situ inorganic acid formation does not have to be compensated for by pH adjustment, since pH's below 4 do not seriously reduce the performance of the reaction system (see Example 2 herein). This simplifies the reaction system and avoids the need to employ buffers.

The process of the present invention is believed to be much less pH dependent than conventional oxygen based systems employing $OsO_4$, because while the osmium-halide reoxidation after reaction is retarded by acid, the transition metal containing co-catalyst reoxidation after reaction is believed to be facilitated at a low pH. Thus, the present invention offers a wide degree of flexibility in terms of pH control.

Furthermore, it will be understood that the use of oxygen as an oxidant in accordance with the process of the present invention, renders it inherently impossible to proceed through a peracid route for hydroxylation (e.g. as in Norton), and inherently assures that the olefins are directly hydroxylated (e.g. through cis-hydroxylation). It will also be understood that the hydroxylation reaction is preferably conducted in the absence of an organic carboyxlic acid such as formic, acetic and propionic acids to avoid possible esterification of the diol product.

In carrying out a preferred embodiment of the invention, olefin, water, oxidant, osmium-halide catalyst (preferably in unsupported form), transition metal containing co-catalyst, and optional inert solvent are contacted by admixing to form a liquid reaction medium in a manner and under conditions sufficient to hydroxylate the olefin, i.e., to directly convert at least one of the ethylenic unsaturations possessed thereby to its corresponding diol. The manner and order of addition of each of the individual components of the liquid reaction medium to the reaction vessel is not critical.

Accordingly, the initial typical reaction medium prior to introduction of olefin and $O_2$ will typically comprise: (a) osmium-halide catalyst in amounts heretofore specified; (b) water subject, to the molar constraints heretofore specified, typically in an amount of from about 5 to about 30 percent, by weight, based on the total weight of the reaction medium; (c) inert organic solvent in an amount of from about 70 to about 95 percent, by weight, based on the weight of the reaction medium.

For the production of ethylene glycol, propylene glycol or any product derived from any unsaturated gaseous olefin, the latter may be bubbled through the reaction mixture containing the components described herein or it may be introduced under pressue. Likewise with the oxygen-containing gas employed as the oxidant. However, it is preferred that the reaction takes place in the liquid phase. Consequently, sufficient pressure is preferably employed to maintain the gaseous reactants in the liquid phase. Otherwise, the reaction pressure is not critical and can be atmospheric, subatmospheric, or super-atmospheric.

When the olefin reactant is a liquid or is dissolved in the reaction mixture under pressure, its concentration in the reaction mixture typically will vary from about 1 to about 98 percent, preferably from about 10 to about 80 percent, and most preferably from about 30 to about 60 percent, by weight, based on the total weight of the reactant mixture inclusive of the weight of components (a) through (b) described above.

The hydroxylation reaction is typically conducted at temperatures which can vary over wide limits although it is preferred to maintain the reaction mixture in the liquid phase in conjunction with the reaction pressure. Accordingly, typical reaction temperatures can vary from about 0 to about 250° C., preferably from about 20 to about 150° C., and most preferably from about 30 to about 130° C. (e.g. 80 to 130° C.).

At temperatures greater than the aforenoted ranges, the reaction rate may increase substantially but this usually occurs at the expense of a reduction in selectivity. At very low reaction temperatures, e.g., below about 0° C. the reaction rate decreases to a commercially undesirable degree. Accordingly, while the reaction temperature is not critical and can vary over a wide range, one normally would not operate at temperature extremes outside the aforenoted ranges.

The hydroxylation reaction can be performed as a batch reaction, as a continuous reaction or as a semicontinuous reaction.

In the batch reaction, a reaction medium containing the above described components is charged into the reaction vessel along with olefin if in liquid form. Alternatively, the reaction vessel is then pressurized with olefin if in gaseous form and oxygen. It may be desirable to heat the liquid reaction mixture to reaction temperature prior to pressurizing with the reactant gases. The reaction is allowed to proceed to the desired degree of completion, typically for a period of from about 0.5 to about 5 hours, preferably from about 0.5 to about 3 hours, and most preferably from about 0.5 to about 2 hours.

In the continuous process, the components can be introduced into the inlet of an elongated reactor at a rate such that substantially complete reaction will have taken place by the time the reaction mixture reaches the reactor outlet. The reaction can be carried out in a semi-continuous manner by metering the reactant mixture components into a series of two or more tank reactors at the appropriate rate to maintain the reactor liquid level.

Additionally, the process may be run in either of the aforementined modes by altering the reaction conditions, and/or, the reactant, solvent, catalyst, co-catalyst concentrations during the course of the reaction. Thus, the process may be run by changing the temperature, pressure, catalyst concentration, oxidant concentration, and/or olefin concentration.

The spent reaction mixture after removal of unreacted olefin is a solution of product glycol, by-products if any, solvent, water, catalyst and co-catalyst. The volatile components are distilled out of the reaction mixture into various fractions leaving non-volatile catalyst components in the still. The product glycol is then separated from the high boiling distillate.

The following examples are given as specific illustrations of the claimed invention. It should be understood, however, that the invention is not limited to the specific details set forth in the examples. All parts and percentages in the examples as well as in the remainder of the specification are by weight unless otherwise specified.

Unless otherwise specified, in the following examples selectivity, conversion and yield are calculated as follows:

$$\% \text{ selectivity} = \frac{\text{moles of glycol formed}}{\text{moles of oxygenated product}} \times 100$$

$$\% \text{ conversion} = \frac{\text{moles of oxygenated product}}{\text{moles of olefin charged}} \times 100$$

$$\% \text{ yield} = \frac{\% \text{ conversion} \times \% \text{ selectivity}}{100}$$

EXAMPLE 1

Into a 300 ml titanium autoclave was charged 0.085 g $OsBr_3$ (0.2 mmole) dissolved in 20 g of a sulfolane:$H_2O$ 4:1 w/w solution, and 1.21 g $CuBr_2$ (5.0 mmole) dissolved in 75 g of a sulfolane:$H_2O$ 4:1 w/w solution. To the autoclave was then added 30.0 g of propylene (710 mmole) and the autoclave contents warmed to 110° C. Oxygen was then added to the reaction mixture from a 300 cc addition vessel to raise the pressure an additional 100 psig and the resulting mixture stirred for 1.0 hour. The reaction mixture was then analyzed for product and found to contain 23.3 mmole of propylene glycol. The selectivity to propylene glycol was therefore about 85% with a conversion based on the moles of propylene of abut 3.3% and a conversion based on oxygen added of 46.6%. The pH of the reaction mixture upon completion of the reaction was 4.5.

EXAMPLE 2

The following example is intended to illustrate the embodiment of the present invention claimed in the above-identified patent application wherein oxygen is employed as the oxidant, but with the external addition of a strong acid (i.e. HBr). The purpose of this run is to show that while the addition of strong inorganic acids is not preferred, the process is nevertheless quite operable at very low pH's.

Accordingly into a 300 ml titanium autoclave was charged $OsBr_3$ (0.09 g, 0.2 mmole), $Cu(NO_3)_2 \cdot 3H_2O$ (1.21 g, 5.0 mmole), and 1.6 g of an aqueous solution containing 47%, by weight, HBr (10.0 mmole) dissolved in 95.4 g of a sulfolane/$H_2O$ (4:1 by weight) solution. Propylene (30 g) was pressured in and the contents warmed to 110° C. Oxygen (60 psig) was then charged and the contents stirred for one hour. The apparent pH before reaction was about 0.5–1 and after reaction completion was about 2.5–3.0. The selectivity to propylene glycol was abut 73% based on propylene charged. This reaction produced 23.0 mmole of propylene glycol. The conversion of propylene was 3% based on propylene added, and 46% based on oxygen added.

COMPARATIVE EXAMPLE 1

The following comparative example is intended to identify the product distribution of Example 2 of Norton, U.S. Pat. No. 3,335,174, Comparative Example 1 of the subject application being run with the only variations from Norton (Ex. 2) being the substitution of glacial acetic acid for the glacial propionic acid (of Norton) and the substitution of 1-octene for the 1-hexene (of Norton).

Accordingly, into a flask, as described and equipped in Example 1, was charged 14.5 ml of a 30 percent, by weight, aqueous solution of $H_2O_2$ and 45 ml of glacial acetic acid and the mixture heated at 75° C. for 1 hour. $OsCl_3$ (0.3 g) was then added to the flask and the solution cooled to 28° C. To this solution was added 1-octene (10 ml) over 10 minutes and the solution cooled with an ice bath to maintain the temperature thereof between 20–30° C. The pH of the solution was 2. After stirring for an additional 20 minutes, the solution was analyzed by gas chromatography. Conversion of $H_2O_2$ was 10 percent, selectivity to 1,2-octanediol was 10 percent, and selectivity to 1,2-octanediacetate was 20 percent.

From the above data, it can be seen that twice as much ester is formed than diol, and the process of Norton is more aptly described as a process for producing esters with diol as a minor by-product, the yield of diol being 1.0%.

The 1% diol yield of Norton clearly does not suggest a viable process for hydroxylating olefins using an osmium-halide catalyst regardless of the oxidant.

Furthermore, it is well known that hydrogen peroxide reacts with organic carboxylic acids to give peracids. Peracids in turn are well known reagents for the epoxidation of olefins. Peracids are also conventionally employed to hydroxylate olefins indirectly, by first carrying out the epoxidation of olefins and then opening the oxirane ring by the action of water in an acid medium. In certain cases, the glycol formed reacts with the carboxylic acid present in the reaction medium and a mixture of mono- and di-esters is formed.

Thus, it is clear that Norton is attempting to utilize a peracid route of olefin oxidations with $H_2O_2$ and osmium halide as, in practical effect, an intermediate epoxidation catalyst as evidenced by the statement therein at Col. 1, Lines 50 et seq., that when short reaction times are used "substantial amounts of epoxide result". Norton, however, cannot control the subsequent esterification of the epoxide-derived diol and hence more ester forms than diol.

EXAMPLE 3

The following example is provided to illustrate that the osmium-halide catalyst described herein is not converted in-situ to $OsO_4$ during reaction.

Thus, Example 1 was repeated and upon completion of the 1 hour reaction period, the product solution was distilled in air up to 85° C. at atmospheric pressure and then under vacuum (25 mm Hg) up to 190° C. No attempt was made to destroy any residual oxidant. The overheads were collected and analyzed for osmium by inductively coupled plasma spectroscopy (ICP) which technique can detect osmium levels as low as 4 parts per billion. No osmium was detected in the overheads.

It is concluded from the above data that if osmium tetroxide (b.p. 130° C.) formed in-situ during above experiment and was present in the reaction mixture which was distilled, the distillation conditions employed in such experiments including temperature and pressure, would necessarily have caused a detectable amount of such osmium tetroxide to volatilize and be present in the overheads analyzed for osmium by the IPC method.

Furthermore, given the low amounts of osmium-halide present in Example 3, even if all of any volatile osmium tetroxide formed in-situ during said runs was caused to be converted to osmium dioxide under reaction conditions, there would still have been sufficient oxidant in contact with said osmium dioxide to cause at least a detectable amount thereof to be reoxidized to the volatile osmium tetroxide during the course of reaction and distillation, thereby causing a detectable amount of osmium tetroxide to volatilize and be present in the analyzed overheads. This also did not happen.

COMPARATIVE EXAMPLE 2

Example 1 was repeated with the exception that $CuBr_2$ was omitted. No propylene glycol or oxygenated product was produced.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the sprirt of the invention.

What is claimed is:

1. A process for hydroxylating at least one olefinic compound having at least one ethylenic unsaturation which comprises reacting said olefinic compound in admixture with water, a molecular oxygen containing oxidant, and an unsupported catalyst composition comprising (i) at least one catalyst (a) being capable of catalyzing said hydroxylation reaction, and (b) being initially added to said admixture as at least one osmium-halide; and (ii) a copper containing co-catalyst; said reaction being conducted in a manner and under conditions sufficient to convert at least one of said ethylenic unsaturation to its corresponding diol.

2. The process of claim 1 wherein said osmium-halide is selected from the group consisting of $Os(X)_n$, $Os(OH)X_3$, $OsOX_4$, $OsO_3X_2$, $OsONX_4$, $(M)_{n'}[OsO_2X_4]^{-2}$, $M^{+1}[Os(OH)X_5]^{-1}$, $(M)_{n'}[OsO_4X_2]^{-2}$, $(M)_{n'}[OsO_2(OH)_2X_2]^{-2}$, $(M)_{n'}[OsNX_5]^{-2}$, and mixtures thereof, wherein said structural formulae: X is at least one halide independently selected from the group consisting of F, Cl, Br, and I; n is an integer of from 3 to 5, M is selected from the group consisting of cations of Li, Na, K, Rb, Cs, Fr, Be, Mg, Ca, Sr, Ba, Ra, $NH_4$, tetrahydrocarbyl ammonium, and tetrahydrocarbyl phosphonium; and n' is a number selected in conjunction with the valence of cation M to achieve a neutral complex.

3. The process of claim 2 wherein the catalyst as admixed is represented by the structural formula $OsX_3$.

4. The process of claim 2 wherein the catalyst as admixed is represented by the structural formula $OsX_4$.

5. The process of claim 2 wherein the catalyst as admixed is represented by the structural formula $OsX_5$.

6. The process of claim 2 wherein the catalyst as admixed is represented by the structural formula $Os(OH)X_3$.

7. The process of claim 2 wherein the catalyst as admixed is represented by the structural formula $OsOX_4$.

8. The process of claim 2 wherein the catalyst as admixed is represented by the structural formula $OsO_3X_2$.

9. The process of claim 2 wherein the catalyst as admixed is represented by the structural formula $OsONX_4$.

10. The process of claim 2 wherein the catalyst as admixed is represented by the structural formula $(M)_{n'}[OsX_6]^{-2}$.

11. The process of claim 2 wherein the catalyst as admixed is represented by the structural formula $(M)_{n'}[OsO_2X_4]^{-2}$.

12. The process of claim 2 wherein the catalyst as admixed is represented by the structural formula $M^{+1}[Os(OH)X_5]^{-1}$.

13. The process of claim 2 wherein the catalyst as admixed is represented by the structural formula $(M)_{n'}[OsO_4X_2]^{-2}$.

14. The process of claim 2 wherein the catalyst as admixed is represented by the structural formula $(M)_{n'}[OsO_2(OH)_2X_2]^{-2}$.

15. The process of claim 2 wherein the catalyst as admixed is represented by the structural formula $(M)_{n'}[OsNX_5]^{-2}$.

16. The process of claim 2 wherein the catalyst is selected from at least one member of the group consisting of $OsF_3$, $OsCl_3$, $OsBr_3$, and $OsI_3$.

17. The process of claim 2 wherein M is a cation represented by the structural formula selected from the group consisting of $(R)_4N^+$, and $(R)_4P^+$ wherein R is a hydrocarbyl group selected from the group consisting of alkyl, aryl, aralkyl and alkaryl.

18. The process of claim 1 wherein said copper containing co-catalyst comprises at least salt selected from the group consisting of copper:halide, porphyrin, pseudohalide, carboxylate, and aryloate.

19. The process of claim 1 wherein the copper containing co-catalyst is soluble in the reaction admixture.

20. The process of claim 1 wherein said reaction is conducted in the presence of a halo-source, and the osmium-halide, copper containing co-catalyst, and halo-source are present in said reaction admixture in an amount sufficient to provide therein a mole ratio of osmium in the osmium-halide:copper metal in said co-catalyst:halogen in said halo-source of from about 1:1:1 to about 1:100:1000.

21. The process of claim 20 wherein said halo-source is derived from halogen present as at least one member selected from the group consisting of osmium-halide, copper halide, alkali metal halide, alkaline earth metal halide, tetrahydrocarbyl ammonium halide, tetrahydrocarbyl phosphonium halide, and Group III-b to VI-b metal halide.

22. The process of claim 21 wherein the halogen of the halo-source is derived from at least one member selected from the group consisting of copper halide, alkaline earth metal halide, and alkali metal halide.

23. The process of claim 1 wherein said reaction is conducted in a liquid reaction mixture provided as a homogeneous solution with respect to catalyst, co-catalyst and reactants, said liquid reaction admixture comprising an inert organic solvent.

24. The process of claim 23 wherein the inert organic solvent is present in said liquid reaction mixture in an amount of from about 20 to about 80%, by weight, based on the weight of the liquid reaction mixture.

25. The process of claim 24 wherein said inert organic solvent is the hydroxylated olefin product.

26. The process of claim 24 wherein the inert organic solvent is dipolar and aprotic.

27. The process of claim 26 wherein said inert organic solvent is selected from the group consisting of sulfolane, acetonitrile, N,N-dimethylacetamide, and N,N-dimethylformamide.

28. The process of claim 1 wherein the olefin contains from 2 to about 20 carbons.

29. The process of claim 1 wherein said hydroxylation reaction is conducted in the absence of an organic carboxylic acid.

30. A process of hydroxylating olefins which comprises admixing in a homogeneous liquid reaction mixture:
   (a) at least one olefin having at least one ethylenic unsaturation;
   (b) at least one molecular oxygen containing gas;
   (c) water;
   (d) at least one osmium-halide capable of catalyzing the hydroxylation of at least one of said ethylenic unsaturation dissolved in said reaction mixture; and
   (e) at least one copper containing co-catalyst dissolved in said reaction mixture;
said admixture being conducted in a manner and under conditions sufficient to convert at least one of said ethylenic unsaturation directly to its corresponding diol.

31. The process of claim 30 wherein the olefin is contacted with the remainder of said components (b) through (d) as a liquid having oxygen dissolved therein.

32. The process of claim 30 wherein the olefin is selected from the group consisting of ethylene, propylene and mixtures thereof.

33. The process of claim 30 wherein water is initially present in said reaction mixture in at least a stoichiometric molar ratio with the molar amount of said ethylenic unsaturation to be hydroxylated.

34. The process of claim 33 wherein water is present in said reaction mixture at a molar ratio of water:olefin ethylenic unsaturation to be hydroxylated, of from about 1:1 to about 100:1.

35. The process of claim 34 wherein water is present in said reaction mixture in an amount sufficient to achieve a mole ratio of water to oxygen in contact with said olefin of from about 1:1 to about 30:1.

36. The process of claim 33 wherein the reaction mixture additionally comprises an inert organic solvent.

37. The process of claim 36 wherein the inert organic solvent is hydroxylated olefin.

38. The process of claim 36 wherein the inert organic solvent is dipolar and aprotic.

39. The process of claim 36 wherein the inert organic solvent is present in said reaction mixture in an amount of from about 20 to about 80%, by weight, based on the total weight of the reaction mixture.

40. The process of claim 30 wherein said reaction mixture also comprises a halo-source in an amount sufficient to provide therein a mole ratio of osmium in the osmium-halide: copper metal in the copper containing co-catalyst:halogen in the halo-source of from about 1:10:100 to about 1:50:500.

41. The process of claim 30 wherein said copper containing co-catalyst is at least one copper halide.

42. The process of claim 41 wherein said co-catalyst is copper bromide.

43. The process of claim 30 wherein the initial pH of said reaction mixture is not less than about 4.

44. The process of claim 43, wherein said initial pH is from about 4 to about 8.

45. The process of claim 30 wherein an organic carboxylic acid is absent from said reaction mixture.

* * * * *